United States Patent [19]

Grassi et al.

[11] Patent Number: 4,556,062

[45] Date of Patent: Dec. 3, 1985

[54] CARDIAC STIMULATOR WITH FREQUENCY SELF-REGULATION THROUGH THE ELECTROCARDIOGRAPHIC T WAVE

[75] Inventors: Gino Grassi, via Imbriani, 21, 50019 Sesto Fiorentino (Firenze); Leonardo Cammilli, Florence; Luciano Alcidi, Florence; Paolo Marconi, Florence, all of Italy

[73] Assignee: Gino Grassi, Sesto Fiorentino, Italy

[21] Appl. No.: 548,775

[22] Filed: Nov. 4, 1983

[30] Foreign Application Priority Data

Nov. 5, 1982 [IT] Italy ................ 9537 A/82

[51] Int. Cl.[4] .............................. A61N 1/30
[52] U.S. Cl. .............................. 128/419 PG
[58] Field of Search ................... 128/419 PG

[56] References Cited

U.S. PATENT DOCUMENTS

| 4,036,690 | 1/1979 | Anderson et al. | 128/419 PG |
| 4,228,803 | 10/1980 | Rickards | 128/419 PG |
| 4,423,733 | 1/1984 | Grassi et al. | 128/419 PG |

FOREIGN PATENT DOCUMENTS

| 17848 | 10/1980 | European Pat. Off. |  |
| 80348 | 6/1983 | European Pat. Off. | 128/419 PG |
| 2334341 | 1/1974 | Fed. Rep. of Germany. |  |
| 2447052 | 4/1975 | Fed. Rep. of Germany. |  |
| 2217235 | 5/1979 | Fed. Rep. of Germany. |  |
| WO81/01659 | 6/1981 | PCT Int'l Appl. |  |

OTHER PUBLICATIONS

*IEEE—Biomedical Engineering*, vol. BME-26, No. 11, Nov. 1979, "T-Waves . . . ", Wolthuis et al., pp. 639–643.
*Soviet Inventions Illustrated*, Derwent, Week D22, Jul. 8, 1981, SU-P3, p. 8, Cardio—Stimulator Controls.

*Primary Examiner*—William E. Kamm
*Attorney, Agent, or Firm*—Cushman, Darby & Cushman

[57] ABSTRACT

A pacemaker used for cardiac stimulation has its stimulation frequency varied according to the changing metabolic requirements of a subject pacemaker user due to stress, emotion and the like. Control of the stimulation frequency is based essentially on the variation in the rising slope of T wave signals from the subject user.

22 Claims, 6 Drawing Figures

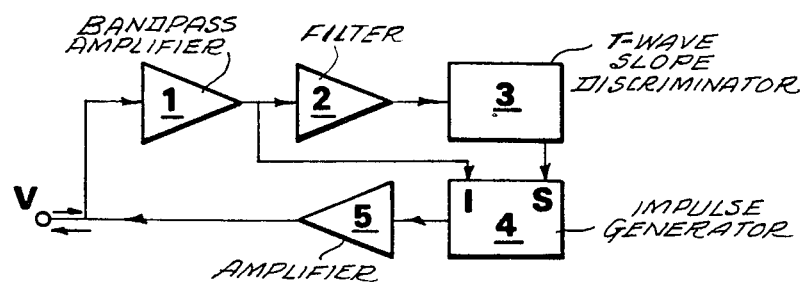
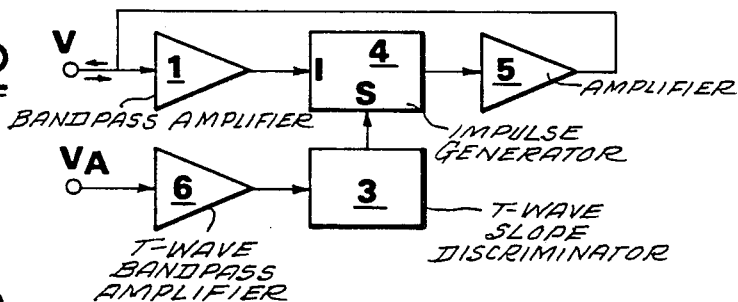
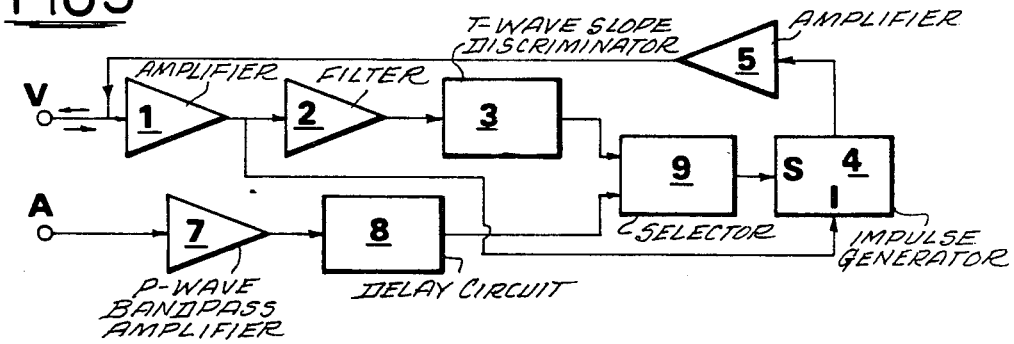
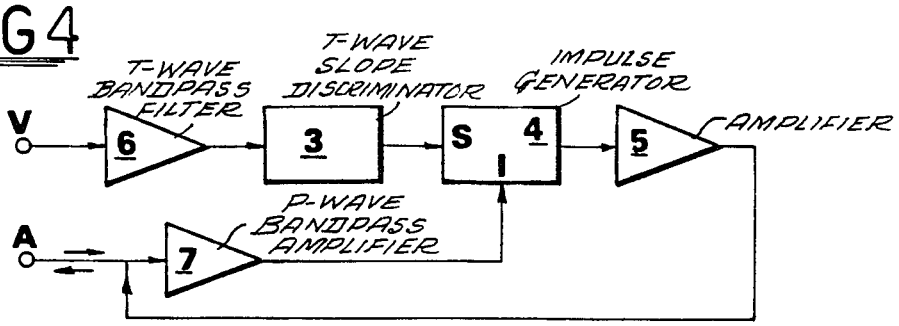

CARDIAC STIMULATOR WITH FREQUENCY SELF-REGULATION THROUGH THE ELECTROCARDIOGRAPHIC T WAVE

BACKGROUND OF THE INVENTION

The invention relates to a cardiac stimulator with frequency self-regulation through the electrocardiographic T wave.

DESCRIPTION OF THE PRIOR ART

As is known, variations in the sympathetic nervous system, such as those that occur during stress, emotion, a state of anxiety, or the use of stimulants (coffee, tobacco), determine modifications in the morphology of the T wave that can increase in amplitude and vary in phase. The said modifications indicate an important biophysiological message of adaptation of the organism to cope with the various situations.

It has been ascertained, through clinical research, that not only in normal patients but also in patients electrostimulated with VV1 pacemakers (and thus at a fixed frequency), a significant variation takes place in the slope of the initial section of the T wave when the exercise test work load is increased. The slope of the curve increases as the work undertaken becomes greater, while with the subsequent recovery it drops back to the initial condition.

The foregoing trend can clearly be seen in intracardiac electrocardiograms.

Another important factor is that if, in the said electrostimulated patient, rises in frequency are programmed in succession, the slope of the T wave remains unaltered when resting but changes with stress.

SUMMARY OF THE INVENTION

The object of the invention is first and foremost to determine an algorithm that can be used for the construction of a pacemaker, the frequency of which is regulated in a physiological fashion.

The said algorithm can be realized in one of the two following forms:

(A) Using a circuit that feels and measures the slope of the initial section of the electrocardiographic T wave and is able to pilot the stimulation frequency of a pacemaker from a pre-established and/or externally programmable minimum frequency, with a pre-established and/or externally programmable factor of proportionality.

(B) Using a circuit as in (A) above, suitably coordinated with another electrical physiological signal, which could be represented by the atrial signal or by the sinus node, when these can normally be obtained.

Both the type A and the type B can be used in pacemakers with atrial and/or ventricular stimulation.

Detection of the T wave can be effected by the stimulating electrode (in the case of ventricular stimulation) and be discriminated by a filter circuit that separates it from the polarization signals existing at the level of the stimulating electrode. Alternatively, it can be detection (and this applies to all types of stimulation) by an electrode placed on the catheter itself, or on a separate one, situated in the ventricle.

BRIEF DESCRIPTION OF THE DRAWINGS

Further details of the cardiac stimulator according to the invention will be given below with reference to the following drawings, in which:

FIG. 1 represents a VV1 stimulator that utilizes one single ventricular V electrode;

FIG. 2 again represents a VV1 stimulator provided with an amplifier connected to an auxiliary ventricular electrode;

FIG. 3 represents the algorithm applied to a VDD stimulator, that is to say one piloted by the atrial signal and inhibited by the ventricular signal;

FIG. 4 represents the algorithm applied to an AA1 atrial stimulator utilized when there is a sino-atrial block with satisfacotry atrio-ventricular conduction;

DESCRIPTION OF THE PREFERRED EMBODIMENT

Figure 5:
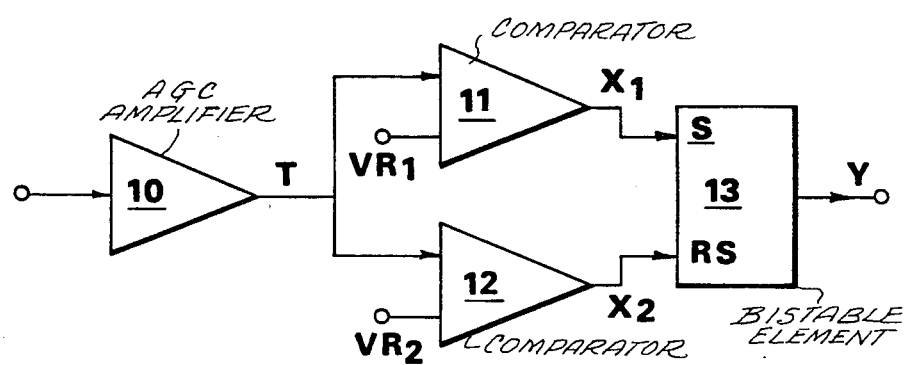
FIG. 5 shows, as an example, a block diagrammatic arrangement for obtaining a signal proportional to the slope of the T wave.

In the block diagram shown in FIG. 1 in respect of a VV1 stimulator that utilizes one single ventricular V electrode, the block 1 consists of a band pass amplifier able to amplify the depolarization QRS waves and the repolarization T wave (3–150 Hz pass band) detected by the V electrode. The block 2 is constituted by a filter that discriminates the said waves from the electrolytic polarization signals present at the electrode-tissue interface after the stimulation impulse. The block 3 is a (dV/dt) T wave slope discriminator, from which issues a signal proportional thereto. The block 4 represents an impulse generator that can inhibit (input I) and can synchronize or pilot in frequency (input S). The block 5 is the amplifier of the ventricular stimulation impulse.

As can be seen, the ventricular cardiac signal is carried to inhibit (from 1 to the input I of 4) the generator when, for normal VV1 operation, the frequency of the said signal exceeds that of the impulse generator.

Contemporaneously, the cardiac signal filtered by 2 is discriminated at 3 in order to obtain the signal proportional to the slope of T which, in turn, pilots the frequency of the impulse generator in accordance with a pre-established and/or programmable rule.

In the event of an absence of spontaneous rhythm, the frequency of the stimulator will vary in this way proportionally with the slope of the T wave and, therefore, proportionally with the metabolic requirements created by the stress to which the patient is subjected.

The further example of a VV1 stimulator is, in FIG. 2, represented by the blocks 1, 4 and 5 to which is added an amplifier 6 connected to an auxiliary ventricular VA electrode having a pass band set for the T wave (3–50 Hz), and this furnishes the signal to the previously described block 3, in turn connected to the input S of the generator 4. The operation of the stimulator is identical to that of the one shown in FIG. 1.

In the example given in FIG. 3 of the application of the algorithm to a VDD stimulator, namely one piloted by the atrial signal inhibited by the ventricular signal, the cardiac signal is picked up by means of a ventricular V electrode with the amplifier 1, through the filter 2 and, therefore, the discriminator 3 of the T wave. Contemporaneously, the intracardiac wave P that is amplified by the amplifier 7 set for this signal (20–200 Hz pass band) is picked up by an atrial electrode A. The atrial signal sets in operation a retard circuit (delay means) 8 that reproduces the natural A-V retard (100–200 msec) and emits a signal upon completion of the said retardation.

The signals forthcoming from 3 and from 8 are utilized by the selection block (selection means) 9 which is set and/or programmed to synchronize the frequency of the generator 4 proportionally with the T wave slope variation and/or to synchronize it with the atrial signal. The ventricular signal is again utilized to inhibit the generator 4 (input I) should the frequency of the natural QRS wave exceed that envisaged at 4. The impulse amplifier 5 carries the stimulus to the ventricular electrode.

In FIG. 4 an example is given of the application of the algorithm to an atrial AA1 stimulator that is utilized when there is a sino-atrial block with satisfactory atrio-ventricular conduction. From the ventricular V electrode, the signal is passed to an amplifier 6 (having the previously described characteristics) and by this to a discriminator 3 that pilots the impulse generator 4. The atrial signal that inhibits the generator 4 when the frequency of the artial wave P exceeds that envisaged at 4, is picked up by the atrial electrode A. Thus it is possible to have atrial stimulation (through the impulse amplifier 5) proportional to the physical or psychic stress to which the patient is subjected.

The examples given above only represent a number of possible applications to which, insofar as this patent is concerned, there is no limit.

The block 3, which is the core of the system, can be constructed with the combination of various components now in common use in the electronics industry.

Figure 6:
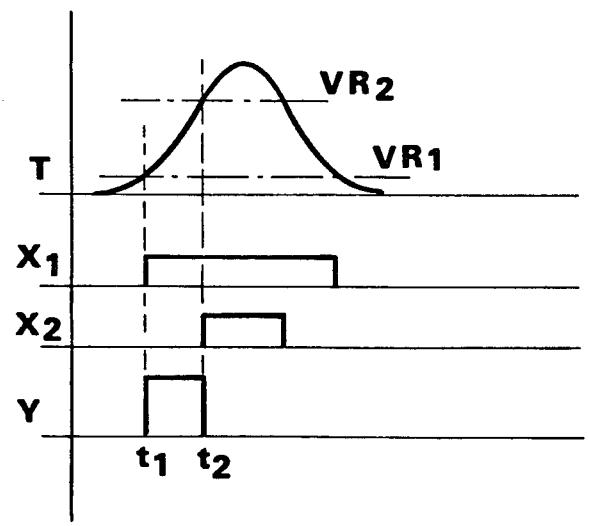
FIG. 6 shows the above mentioned signal sent to two fixed reference signal comparators, one of which corresponding to a minimum level and the other to a maximum level.

In FIG. 5, by way of an example, a block diagrammatic arrangement is shown for obtaining a signal proportional to the slope of the T wave. This envisages there being an amplifier 10 provided with a system for automatically regulating the gain in such a way as to obtain an output signal that is always of the same amplitude. The signal thus obtained is sent to two fixed reference signal comparators, one corresponding to a minimum level 11 and one to a maximum level 12 of the signal (FIG. 6). These furnish two time staggered output signals, $X_1$ and $X_2$, respectively, the former at $t_1$ and the latter at $t_2$, the $t_2-t_1$ interval being proportional to the slope of the examined wave.

The said two signals can be sent to the input of a bistable circuit that will furnish an output signal Y, the duration of which is again proportional to the slope.

In order to discriminate the T wave from other cardiac signals, use can be made, for example, of a circuit for quenching the amplifier whereby it be left open only at a time corresponding to that of appearance of the T wave (for example, between 150 and 400 msec after the spike).

What is claimed is:

1. A method for controlling the stimulation pulse rate of a cardiac pacemaker, comprising the steps of:
    sensing T-wave repolarization signals from a subject using the pacemaker;
    determining the slope of the sensed T-wave signals; and
    adjusting the stimulation pulse rate of the pacemaker in proportion to the determined slope of the sensed T-wave signals, thereby adjusting the stimulation pulse rate of the pacemaker to metabolic requirements of the subject user.

2. A method as in claim 1, wherein the T-wave signals are sensed and the stimulation pulses are output through a single ventricular electrode.

3. A method as in claim 1, wherein the adjusting step includes the steps of increasing the stimulation pulse rate with relatively increased T-wave signal slopes, decreasing the stimulation pulse rate with relatively decreased T-wave signal slopes and holding the present stimulation pulse rate in response to non-changed T-wave signal slopes.

4. A method as in claim 3, further including the steps of:
    sensing all ventricular cardiac signals of the subject; and
    limiting the increase of the stimulation pulse rate to the repetition rate of the sensed ventricular cardiac signals.

5. A method as in claim 4, further comprising the steps of:
    providing a first centricular electrode for sensing all ventricular cardiac signals and for outputting the stimulation pulses to the subject from the pacemaker; and
    providing a second ventricular electrode for sensing the T-wave signals.

6. A method as in claim 4, further comprising the steps of:
    providing an atrial electrode for sensing P-wave signals from the subject;
    delaying the sensed P-wave signals to establish a naturally-occurring time sequence of the P-wave and T-wave signals; and
    adjusting the stimulation pulse rate also in response to the delayed sensed P-wave signals.

7. A method as in claim 3, further comprising the steps of:
    providing a ventricular electrode for sensing the T-wave signals from the subject;
    providing an atrial electrode for sensing P-wave signals from the subject and for outputting the stimulation pulses from the pacemaker to the subject; and
    limiting the increase of the stimulation pulse rate to the repetition rate of the sensed P-wave signals.

8. A method as in claim 1, wherein said determining step includes the step of determining the rising slope of the sensed T-wave signals.

9. A method of controlling the cardiac pacemaker, comprising the step of adjusting the stimulation pulse rate of the pacemaker in accordance with the T-wave signal morphology of a user of the pacemaker.

10. A cardiac pacemaker for use with a patient comprising:
    sensing means for sensing ventricular cardiac signals from said patient;
    filter means, responsive to said sensing means, for extracting T-wave signals from said sensed cardiac signals;
    slope discriminator means, responsive to said filter means, for discriminating the rising slope of said extracted T-wave signals;
    impulse generator means, responsive to said slope discriminator means, for outputting to said patient stimulation pulses having a frequency varying in proportion with said T-wave signal slopes, wherein the T-wave signal slopes are indicative of metabolic requirements of said patient, and the pacemaker thus is responsive to changing metabolic requirements of the patient.

11. A pacemaker as in claim 10, wherein said impulse generator means includes inhibit means for limiting variation of said stimulation pulse frequency to no frequency greater than the frequency of said sensed ventricular cardiac signals.

12. A pacemaker as in claim 11, further comprising:
P-wave sensing means for sensing P-wave signals from said sensing means; and
delay means, responsive to said P-wave sensing means, for variably delaying said sensed P-wave signals; wherein
said impulse generator means includes means for adjusting said stimulation pulse frequency in response to said delayed sensed P-wave signals.

13. A pacemaker as in claim 18, wherein said sensing means includes first sensing means for sensing said ventricular cardiac signals and auxiliary sensing means for sensing only T-wave signals from said patient.

14. A pacemaker as in claim 10, wherein
said sensing means includes ventricular electrode means for sensing said ventricular cardiac signals and atrial electrode means for sensing P-wave signals from said patient; and
said impulse generator means includes inhibit means for limiting the variation of said stimulation pulse frequency to no frequency greater than the frequency of said sensed P-wave signals.

15. A pacemaker as in claim 10, wherein said discriminator means comprises:
AGC amplifier means for maintaining within a predetermined range the amplitude-level of the said extracted T-wave signals, and outputting the same;
first and second comparator means for comparing first and second reference signals, respectively, to said AGC amplifier means output; and
bistable means, responsive to said comparator means, for outputting a pulse width modulated signals whose width varies in accordance with said rising slope of said T-wave signals.

16. A cardiac pacemaker having a variable stimulation pulse rate for use with a patient comprising:
means for developing T-wave signals based upon cardiac signals of said patient; and
means for adjusting said stimulation pulse rate in proportion to the slope of said developed T-wave signals, thereby adjusting said stimulation pulse rate of said pacemaker to metabolic requirements of said patient.

17. A pacemaker as in claim 16, further comprising a ventricular electrode means for sensing said cardiac signals and for outputting the stimulation pulses from said pacemaker to said patient.

18. A pacemaker as in claim 16, wherein said adjusting means includes means for increasing said stimulation pulse rate with relatively increased T-wave signal slopes, for decreasing said rate with relatively decreased slopes and for holding the present rate with relatively unchanged slopes.

19. A pacemaker as in claim 18, further including:
first means for sensing all ventricular cardiac signals of said patient; and
means for limiting increase of said stimulation pulse rate to the repetition rate of said sensed ventricular cardiac signals.

20. A pacemaker as in claim 19, further comprising:
atrial electrode means for sensing P-wave signals from said patient;
delay means for delaying said sensed P-wave signals to establish a naturally-occurring time sequence of said P-wave and T-wave signals; and
means for adjusting said stimulation pulse rate also in accordance with said delayed sensed P-wave signals.

21. A pacemaker as in claim 18, further comprising:
atrial electrode means for sensing P-wave signals from said patient; and
means for limiting increase of said stimulation pulse rate to the reptition rate of said sensed P-wave signals.

22. A pacemaker as in claim 16, wherein said adjusting means includes means responsive to the rising slope of said T-wave signals.

* * * * *